(12) United States Patent
Kishi

(10) Patent No.: US 9,737,996 B2
(45) Date of Patent: Aug. 22, 2017

(54) LINEAR DRIVING MECHANISM WITH SELF-WEIGHT COMPENSATION, OPERATION INPUT DEVICE, AND SURGERY ASSISTANCE SYSTEM

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 338 days.

(21) Appl. No.: 14/565,863

(22) Filed: Dec. 10, 2014

(65) Prior Publication Data

US 2015/0090065 A1    Apr. 2, 2015

Related U.S. Application Data

(63) Continuation of application No. PCT/JP2013/066327, filed on Jun. 13, 2013.

(30) Foreign Application Priority Data

Jun. 13, 2012  (JP) ................................ 2012-133547

(51) Int. Cl.
  *B25J 19/00* (2006.01)
  *B25J 13/02* (2006.01)
  (Continued)

(52) U.S. Cl.
  CPC ............ *B25J 19/002* (2013.01); *A61B 34/30* (2016.02); *A61B 34/37* (2016.02); *A61B 34/74* (2016.02);
  (Continued)

(58) Field of Classification Search
  CPC .. B25J 19/002; B25J 3/04; B25J 13/02; A61B 34/30; A61B 34/37
  See application file for complete search history.

(56) References Cited

U.S. PATENT DOCUMENTS 4,598,601 A * 7/1986 Molaug ................ B25J 19/0016
                                                  248/648
5,257,998 A * 11/1993 Ota ........................ A61B 90/11
                                                  414/917

(Continued)

FOREIGN PATENT DOCUMENTS

JP       S57-034389 U    2/1982
JP       61-071987 A     4/1986
              (Continued)

OTHER PUBLICATIONS

International Search Report dated Sep. 3, 2013 issued in PCT/JP2013/066327.

(Continued)

*Primary Examiner* — David M Fenstermacher
(74) *Attorney, Agent, or Firm* — Scully, Scott, Murphy & Presser, P.C.

(57) ABSTRACT

When the mass of the first moving body is defined as M1, the mass of the second moving body is defined as M2, the distance between a first intersection point of a perpendicular line from a rotation center of the rotation axis to the first moving body and a first gravity center of the first moving body when the distance between the first intersection point and the first gravity center in the first moving body is the shortest is defined as L1, and the distance between a second intersection point of a perpendicular line from the rotation center of the rotation axis to the second moving body and a second gravity center of the second moving body when the distance between the second intersection point and the second gravity center in the second moving body is the shortest is defined as L2, $M2=(L1/L2) \times M1$ is satisfied.

9 Claims, 6 Drawing Sheets

(51) Int. Cl.
  *B25J 3/04*       (2006.01)
  *G05G 5/02*       (2006.01)
  *G05G 23/02*      (2006.01)
  *G05G 9/047*      (2006.01)
  *A61B 34/30*      (2016.01)
  *A61B 34/37*      (2016.01)
  *A61B 34/00*      (2016.01)
  *A61B 90/50*      (2016.01)

(52) U.S. Cl.
  CPC ........... *B25J 3/04* (2013.01); *B25J 13/02* (2013.01); *G05G 5/02* (2013.01); *G05G 9/04737* (2013.01); *G05G 23/02* (2013.01); *A61B 2090/504* (2016.02); *A61B 2090/5025* (2016.02); *Y10T 74/20396* (2015.01)

(56) References Cited

U.S. PATENT DOCUMENTS

| | | | |
|---|---|---|---|
| 6,210,097 | B1 | 4/2001 | Kim et al. |
| 6,354,167 | B1* | 3/2002 | Snow ............... B25J 9/042 248/648 |
| 6,436,107 | B1 | 8/2002 | Wang et al. |
| 2009/0088897 | A1* | 4/2009 | Zhao ............... G06K 9/3216 700/250 |
| 2010/0154579 | A1* | 6/2010 | Nakamura ........... B25J 9/102 74/490.05 |
| 2011/0126660 | A1* | 6/2011 | Lauzier ........... B25J 17/0208 74/490.05 |
| 2012/0312186 | A1* | 12/2012 | Shasha ............... A63G 1/30 104/93 |
| 2015/0239133 | A1* | 8/2015 | Whitney ........... B25J 19/002 74/490.01 |
| 2015/0274447 | A1* | 10/2015 | McCollum ......... B25J 9/0093 414/792.6 |
| 2015/0360882 | A1* | 12/2015 | Girtman ............. B65G 59/02 700/213 |

FOREIGN PATENT DOCUMENTS

| | | |
|---|---|---|
| JP | 02-004778 U | 1/1990 |
| JP | H02-298480 A | 12/1990 |
| JP | 04-122583 A | 4/1992 |
| JP | H07-197960 A | 8/1995 |
| JP | 09-272082 A | 10/1997 |
| JP | 2001-002398 A | 1/2001 |
| JP | 2007-098507 A | 4/2007 |
| JP | 4144021 B | 9/2008 |
| JP | 2011-098821 A | 5/2011 |
| JP | 2011-152176 A | 8/2011 |

OTHER PUBLICATIONS

Extended Supplementary European Search Report dated Mar. 4, 2016 in related European Application No. 13 80 1424.9.
Extended Supplementary European Search Report dated Mar. 4, 2016 in related European Application No. 13 80 4124.9.
Japanese Office Action dated Jul. 5, 2016 in related Japanese Patent Application No. 2012-133547.

\* cited by examiner

LINEAR DRIVING MECHANISM WITH SELF-WEIGHT COMPENSATION, OPERATION INPUT DEVICE, AND SURGERY ASSISTANCE SYSTEM

This application is a continuation application based on PCT/JP2013/066327, filed on Jun. 13, 2013, claiming priority based on Japanese Patent Application No. 2012-133547, filed in Japan on Jun. 13, 2012. The contents of both the Japanese Patent Application and the PCT Application are incorporated herein by reference.

TECHNICAL FIELD

The present invention relates to a linear driving mechanism with self-weight compensation, an operation input device, and a surgery assistance system.

BACKGROUND ART

In the related art, master-slave type remote operation devices have been known as devices for performing remote operation. Generally, the master-slave type remote operation devices have an operation input device that allows an operator to perform an operation input and an actuation unit that is actuated by a command from the operation input device. In this case, it is known that a spring, an actuator, or a counter weight is used in order to compensate for the self-weight of the operation input device or the actuation unit to reduce the load during actuation.

For example, Japanese Unexamined Patent Application, First Publication No. H9-272082 discloses compensating self-weight using a constant tension spring. Additionally, Japanese Unexamined Patent Application, First Publication No. 2007-98507 discloses compensating self-weight using a motor. Moreover, Japanese Patent Publication No. 4144021 discloses compensating self-weight using a link and a spring.

SUMMARY OF THE INVENTION

A linear driving mechanism with self-weight compensation according to a first aspect of the present invention includes a holding member that holds a first moving body to which an object is attached, a second moving body provided with a weight, and a coupling portion that couples the first moving body to the second moving body so that the weight moves with a directional component in a direction opposite to a movement direction of the first moving body. The holding member is capable of rotating around a rotation axis. When a mass of the first moving body in a state where the object is attached is defined as $M1$, a mass of the second moving body is defined as $M2$, a distance between a first intersection point of a perpendicular line from a rotation center of the rotation axis to the first moving body and a first gravity center of the first moving body when the distance between the first intersection point and the first gravity center in the first moving body is the shortest is defined as $L1$, and a distance between a second intersection point of a perpendicular line from the rotation center of the rotation axis to the second moving body and a second gravity center of the second moving body when the distance between the second intersection point and the second gravity center in the second moving body is the shortest is defined as $L2$, $M2=(L1/L2) \times M1$ is satisfied.

According to a second aspect based on the first aspect, the first moving body and the second moving body may linearly move in directions that are parallel to each other and opposite to each other.

According to a third aspect based on the first or second aspect, the first moving body may have a first rack extending in a direction of a straight line connecting the first intersection point and the first gravity center in the first moving body, the second moving body may have a second rack extending in a direction of a straight line connecting the second intersection point and the second gravity center in the second moving body, and the coupling portion may have a gear unit that engages with the first rack and the second rack.

According to a fourth aspect based on the third aspect, the gear unit may have a first gear that engages with the first rack; and a second gear that engages with the second rack, and when a first radius of the first gear is defined as $d1$ and a second radius of the second gear is defined as $d2$, $M2=(L1/L2) \times M1 = (d1/d2) \times M1$ may be satisfied.

According to a fifth aspect of the present invention based on any one of the first to fourth aspects, the rotation center may be near the gravity center of the holding member.

An operation input device according to a sixth aspect of the present invention includes the linear driving mechanism with self-weight compensation according to any one of the first to fifth aspects; a base coupled to the linear driving mechanism with self-weight compensation; an abutment portion that is provided at the base and is capable of abutting against a portion of the first moving body; and a relative value type detector that detects a movement distance or a position of at least any one of the first moving body, the second moving body, and the coupling portion. The detector may be initialized in a positional relationship in which the first moving body has abutted against the abutment portion.

A surgery assistance system according to a seventh aspect of the present invention includes the operation input device according to the sixth aspect; and an actuation unit that has a surgical instrument for performing surgery on a patient, is connected to the operation input device, and is actuated at least on the basis of a movement distance or a position detected in the detector.

DESCRIPTION OF EMBODIMENTS (First Embodiment)

Figure 1:
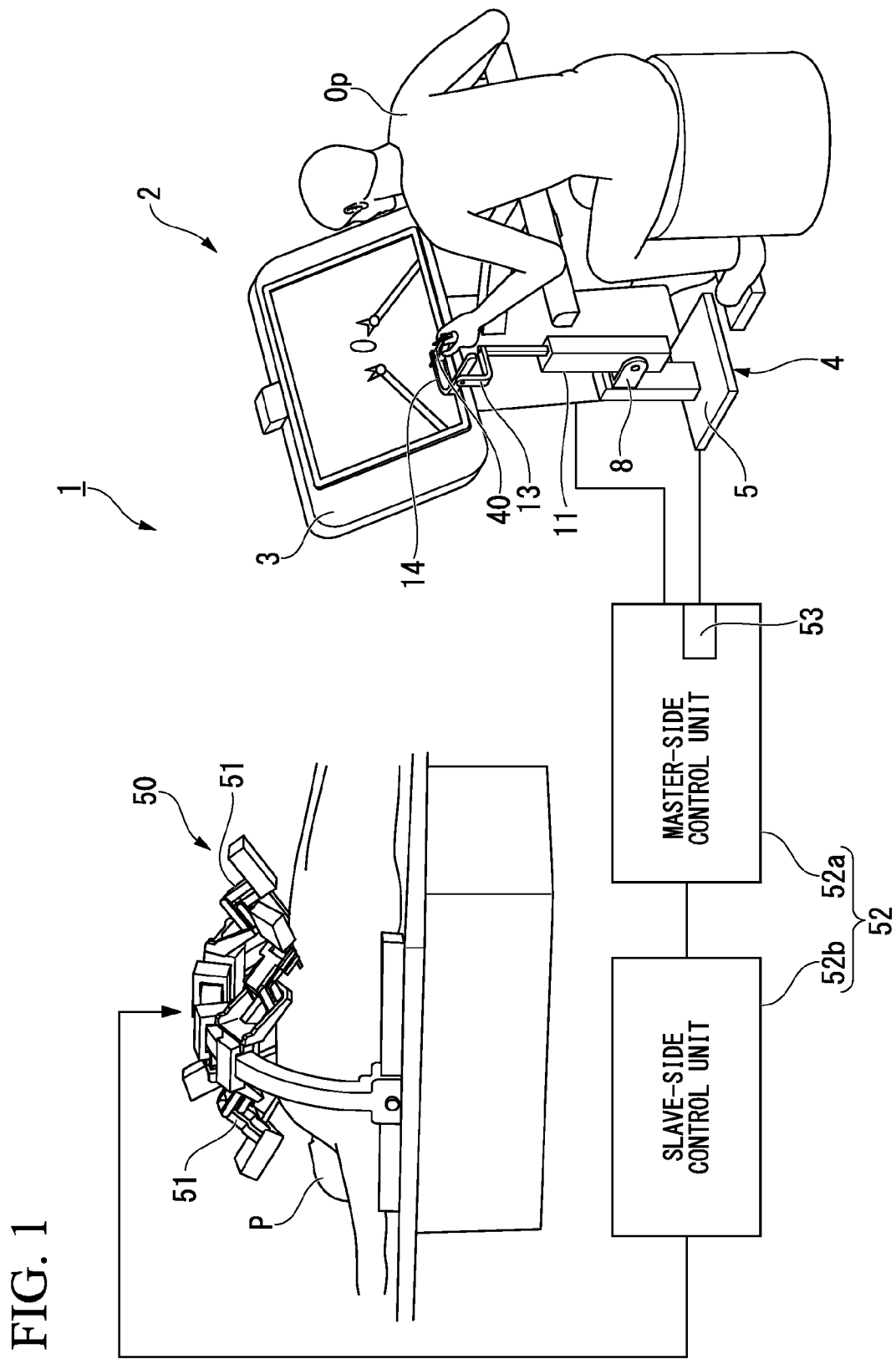
FIG. 1 is an overall view illustrating a surgery assistance system of a first embodiment of the present invention.
Figure 2:
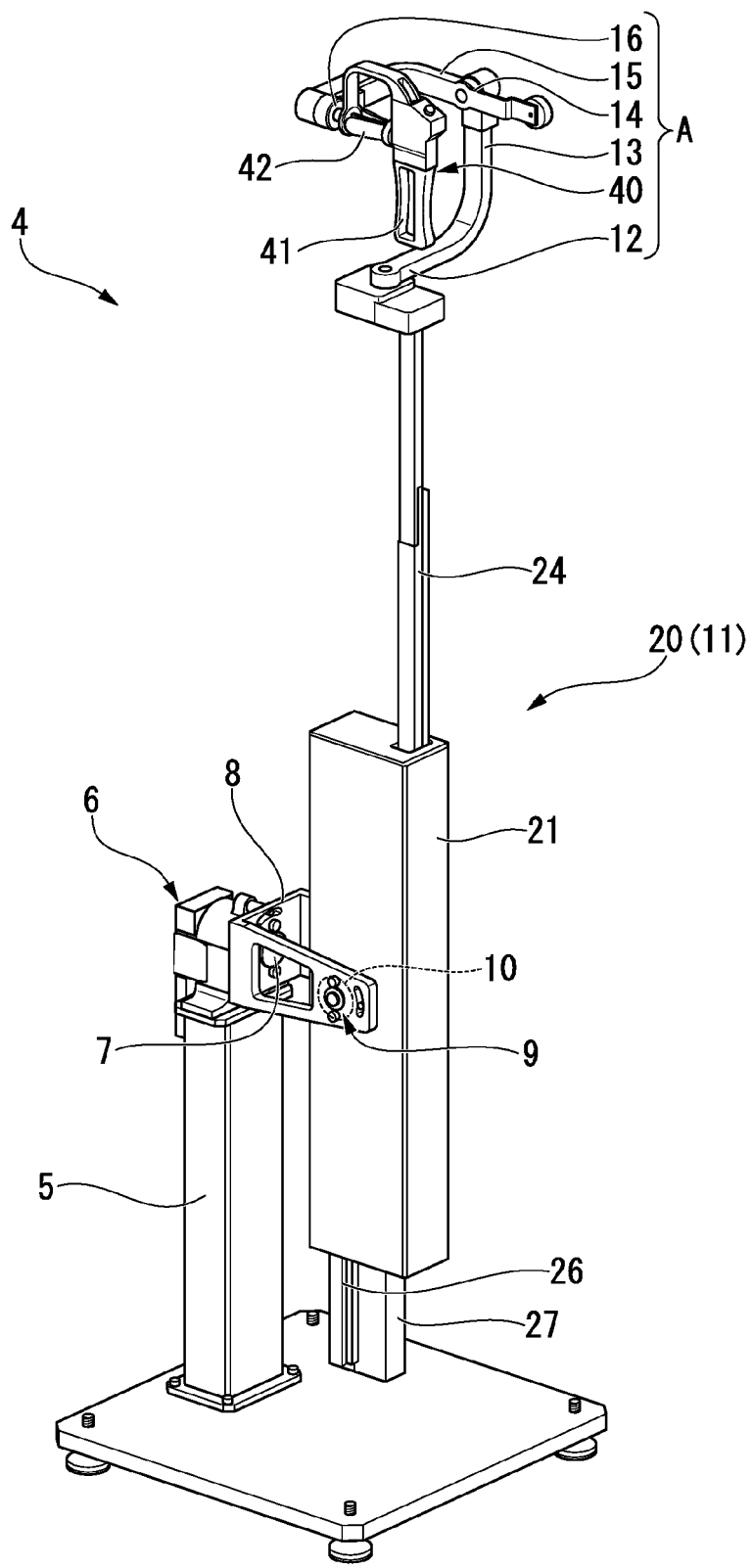
FIG. 2 is a perspective view illustrating the configuration of an operation unit in a master operation input device provided in the surgery assistance system of the first embodiment of the present invention.
Figure 3:
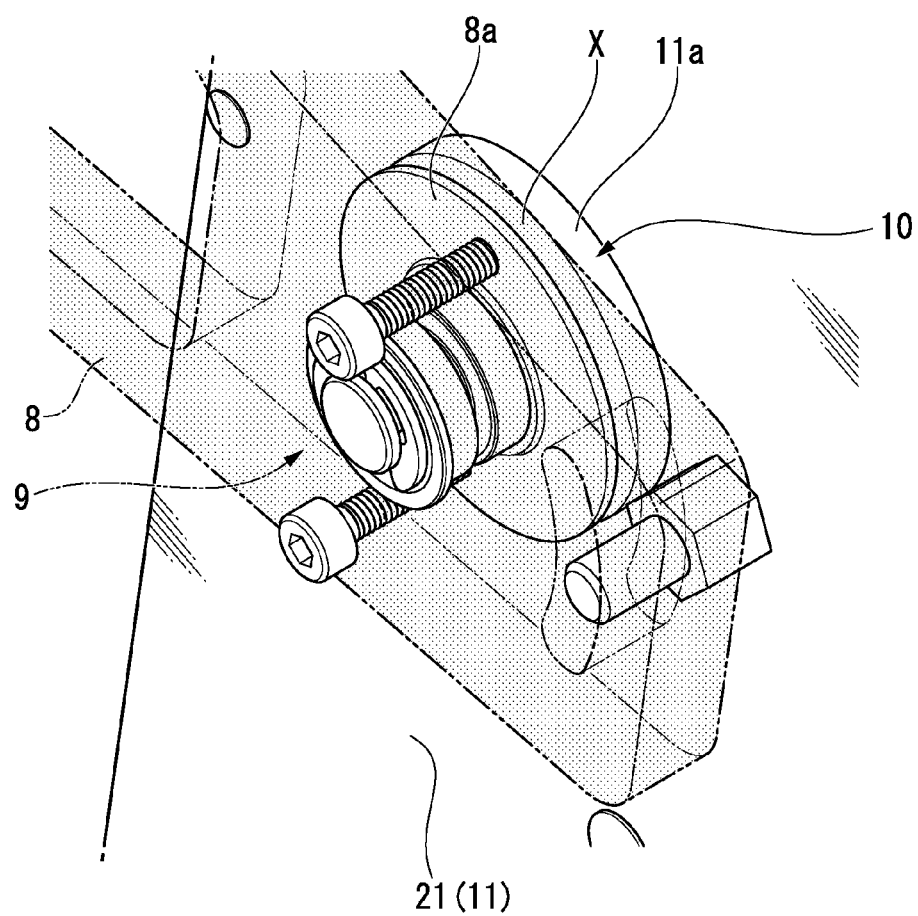
FIG. 3 is an enlarged view illustrating a portion of a linear driving mechanism of the first embodiment of the present invention.
Figure 4:
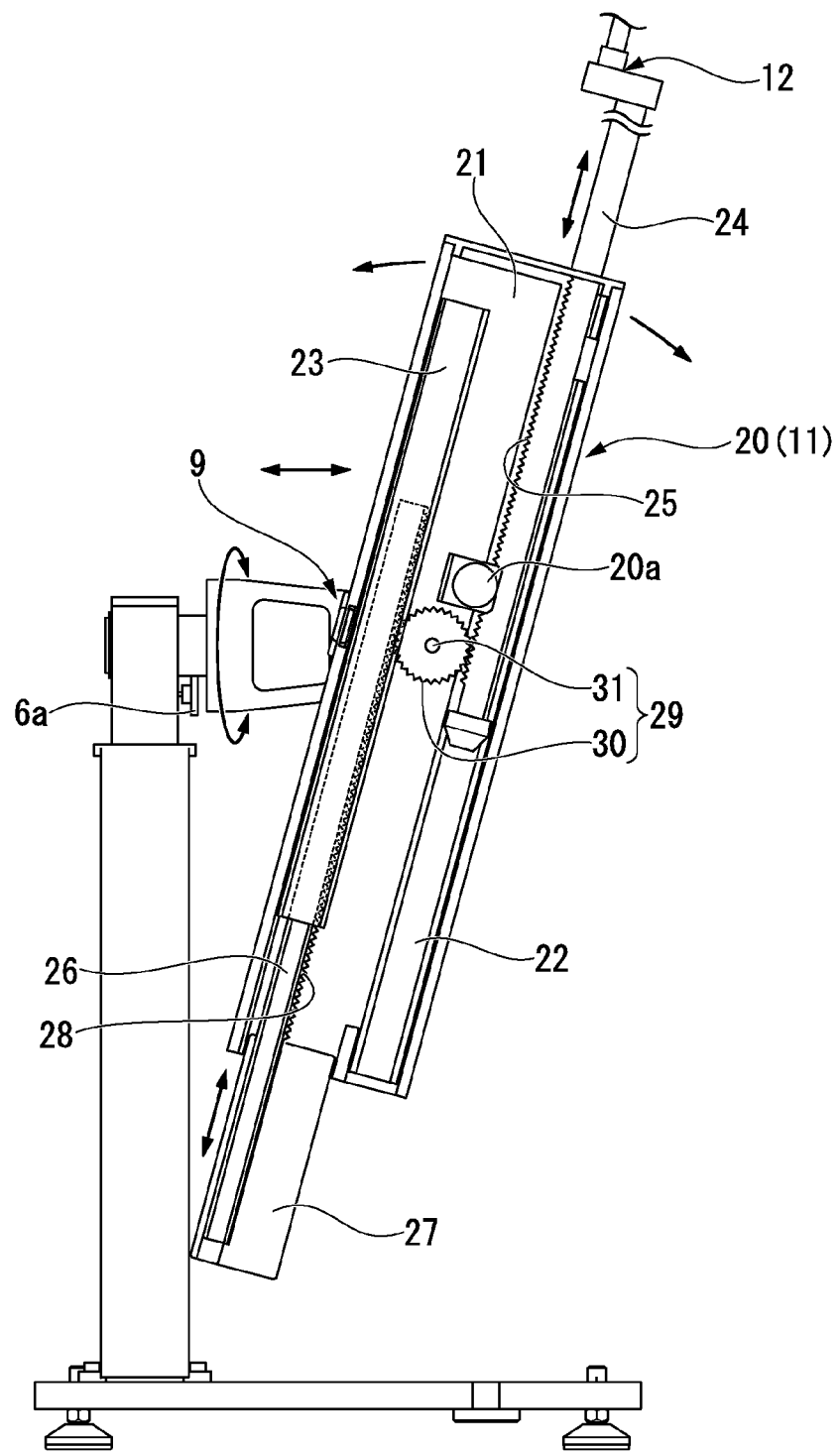
FIG. 4 is a view illustrating the internal structure of the linear driving mechanism in the operation unit of the first embodiment of the present invention.

A linear driving mechanism with self-weight compensation (hereinafter simply referred to as a "linear driving mechanism"), an operation input device, and a surgery assistance system of a first embodiment of the present invention will be described. FIG. 1 is an overall view illustrating the surgery assistance system of the present embodiment. FIG. 2 is a perspective view illustrating the configuration of an operation unit in a master operation input device provided at the surgery assistance system. FIG. 3 is an enlarged view illustrating a portion of the linear driving mechanism. FIG. 4 is a view illustrating the internal structure of the linear driving mechanism.

As shown in FIG. 1, the surgery assistance system 1 is a master-slave type surgery assistance system, and includes a master operation input device 2 (operation input device), a slave manipulator 50 (actuation unit), and a control unit 52.

The master operation input device 2 functions as a master that transmits the movement of an operator Op to the slave manipulator 50, and includes a display unit 3 and an operation unit 4.

The display unit 3 displays an image of a patient P's surgery site and its vicinity taken by a camera (not shown). As the display unit 3, well-known display units, such as a liquid crystal display and an organic electroluminescent display, can be selected appropriately, and can be adopted.

As shown in FIG. 1, the operation unit 4 is communicably connected to the control unit 52, and is arranged on a front side of the display unit 3 so that the operator Op can perform an operation while viewing the display unit 3. Although not shown, in the present embodiment, operation units 4 are respectively provided on the right-hand side and left-hand side of the operator Op. As the operator Op grips a grip unit 40 of the operation unit 4, position and orientation information of the operation unit 4 is input to a position and orientation detector 53 to be described below. It is desirable that the operation unit 4 generally have six degrees of freedom. As long as only position information is input to the position and orientation detector 53, the operation unit 4 may have three degrees of freedom.

As shown in FIG. 2, the operation unit 4 includes a base 5, a first arm 8 coupled to the base 5 via a first joint 6, a holding member 21 coupled to the first arm 8 via a second joint 9, a first moving body 24 that performs a linear motion with respect to the holding member 21 via a third joint 11, a second arm 13 coupled to the first moving body 24 via a fourth joint 12, a third arm 15 coupled to the second arm 13 via a fifth joint 14, and a grip unit 40 coupled to the third arm 15 via a sixth joint 16.

The first joint 6 is a joint that makes the first arm 8 rotatable with respect to the base 5 around a rotational axis extending in a horizontal direction.

The second joint 9 is a joint that makes the holding member 21 rotatable with respect to the first arm 8 around a rotational axis orthogonal to the rotational axis of the first joint 6.

The third joint 11 is a linear motion joint that allows the first moving body 24 to advance and retreat with respect to the holding member 21 in a direction orthogonal to the rotational axes of the second joint 9 and the first joint 6.

The fourth joint 12 is a joint that makes the second arm 13 rotatable with a linear motion axis direction of the third joint 11 as a rotational axis.

The fifth joint 14 is a joint that makes the third arm 15 rotatable with respect to the second arm 13 around a rotational axis orthogonal to the rotational axis of the fourth joint 12.

The sixth joint 16 is a joint that makes the grip unit 40 rotatable with respect to the third arm 15 around a rotational axis orthogonal to the rotational axis of the fifth joint 14.

By using the first joint 6, the second joint 9, and the third joint 11, with a point where the rotational axes of the first joint 6 and the second joint 9 intersect each other as a center, a three-dimensional polar coordinate system can be established and the position of a tip portion of the first moving body 24 can be determined.

By arranging the grip unit 40 near a position where the rotational axes of the fourth joint 12, the fifth joint 14, and the sixth joint 16 intersect each other, a gimbal structure is obtained and a orientation can be input without changing a position with respect to the fourth joint 12.

That is, the grip unit 40 is arranged so that the rotational axes of the fourth joint 12, the fifth joint 14, and the sixth joint 16 intersect each other on an axis that passes through the intersection point of the rotational axes of the first joint 6 and the second joint 9 and is parallel to the linear motion axis of the third joint. Accordingly, the position of the grip unit 40 can be calculated from the movement distances of the first joint 6, the second joint 9, and the third joint 11.

The linear driving mechanism with self-weight compensation of the present embodiment has a configuration in which the operativity of the grip unit 40 is prevented from being impaired by compensating self-weight irrespective of the movement distances of the respective joints, even if the position of the grip unit 40 is moved.

As shown in FIGS. 2 and 3, the first joint 6 and the second joint 9 are respectively provided with brakes 7 and 10 that apply slight resistance during the rotation of the respective joints. For example, as shown in FIG. 3, the brake 10 provided at the second joint 9 has a first pressing plate 8a fixed to the first arm 8 and a second pressing plate 11a fixed to the holding member 21, and generates sliding resistance as the first pressing plate 8a and the second pressing plate 11a come into contact with each other via a pad X, such as felt or rubber. The brake 7 provided at the first joint 6 also has a configuration in which sliding resistance is generated according to the same principle as that of the brake 10 provided at the second joint 9. In addition, the respective brakes 7 and 10 may be adapted to be able to adjust the magnitude of the sliding resistances.

As shown in FIG. 4, the holding member 21 includes the third joint 11 that changes the distance between the second joint 9 and the fourth joint 12. The third joint 11 includes the first moving body 24, a second moving body 26, and a coupling portion 29.

The holding member 21 is a hollow member coupled to the first arm 8 via the second joint 9. A portion of the first moving body 24, a portion of the second moving body 26, and the coupling portion 29 are disposed inside the holding member 21. Additionally, a first guide 22 that holds the first moving body 24 so as to be able to advance and retreat, and a second guide 23 that holds the second moving body 26 so as to be able to advance and retreat are provided within the holding member 21. In the present embodiment, both the first guide 22 and the second guide 23 are fixed to an internal surface of the holding member 21. Additionally, the first guide 22 and the second guide 23 are disposed so as to be parallel to each other.

The holding member 21 is rotatable around the second joint 9 as a rotation axis. The position of the aforementioned rotation axis in the holding member 21 is near the gravity center of the holding member 21. The position of the rotation axis for rotating the holding member 21 may be shifted as long as the position is within a range where the frictional force of the holding member 21 is balanced with the frictional force of the first arm 8. For example, the position may be shifted about 1 cm or 2 cm from the gravity center of the holding member 21.

The first moving body 24 is formed in the shape of a rod, and is provided in a state where one end of the first moving body 24 protrudes from the holding member 21. The above-described fourth joint 12 is attached to a protruding end of the first moving body 24. In the present embodiment, the respective constituent elements (refer to FIG. 2) ranging from the second arm 13 to the grip unit 40 are an object A, which is attached to the first moving body 24.

As shown in FIG. 4, the first moving body 24 has a rack 25 (first rack) extending in a length direction of the first moving body 24 (extending in the direction of a straight line connecting a first intersection point and a first gravity center, which will be described below, in the first moving body 24).

The second moving body 26 is formed in the shape of a rod and disposed parallel to the first moving body 24. A weight 27 having a predetermined mass is fixed to the second moving body 26. The weight 27 is a balance weight for the object. The second moving body 26 has a rack 28 (second rack) extending in a length direction of the second moving body 26 (extending in the direction of a straight line connecting a second intersection point and a second gravity center (to be described below) in the second moving body 26).

The coupling portion 29 couples the first moving body 24 and the second moving body 26 so that the weight 27 moves with a directional component in a direction opposite to a movement direction of the first moving body 24. The coupling portion 29 of the present embodiment includes a pinion 30 (gear unit) that engages with the rack of the first moving body 24 and engages with the rack of the second moving body 26, and a shaft body 31 that rotatably supports the pinion 30. The pinion 30 is supported by the holding member 21 via the shaft body 31. That is, in the present embodiments, the first moving body 24, the second moving body 26, and the coupling portion 29 are configured so as to have parallel shaft gears. Since the first moving body 24 and the second moving body 26 are coupled via the pinion 30 in this way, the first moving body 24 and the second moving body 26 linearly move in directions that are parallel to each other and opposite to each other. In the present embodiment, an absolute value of the linear movement distance of the first moving body 24 and an absolute value of the linear movement distance of the second moving body 26 are equal to each other.

Figure 5:
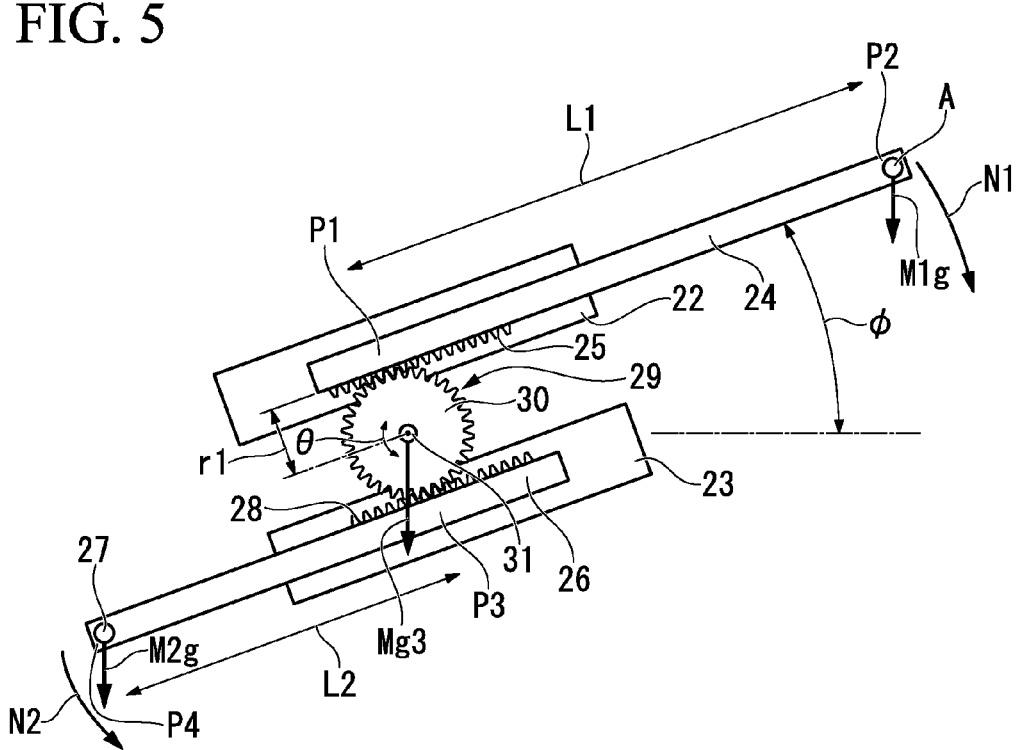
FIG. 5 is a schematic view of a linear driving mechanism with self-weight compensation provided at the linear driving mechanism of the first embodiment of the present invention.

FIG. 5 is a schematic view of the third joint 11 provided at the holding member 21.

The position and mass of the weight 27 fixed to the second moving body 26 are set so that moments N1 and N2 of forces that are schematically shown in FIG. 5 are balanced with each other. That is, when the mass of the first moving body 24 in a state where the object A is attached is defined as M1, the mass of the second moving body 26 including the weight 27 is defined as M2, the foot position of a perpendicular line from a rotation center of the second joint 9 to a linear motion axis of the first moving body 24 is defined as P1 (first intersection point), the gravity center position of the object A and the first moving body 24 is defined as P2 (first gravity center), the foot position of a perpendicular line from a rotation center of the second joint 9 to a linear motion axis of the second moving body 26 is defined as P3 (second intersection point), the gravity center position of the second moving body 26 including the weight 27 is defined as P4 (second gravity center), the distance between the position P1 and the position P2 when the first moving body 24 is in an initial position state (the distance between the first gravity center and the first intersection point in the first moving body 24 when the distance between the first intersection point of the perpendicular line from the rotation center of the rotation axis to the first moving body 24 and the first gravity center of the first moving body 24 is the shortest, to be described below) is defined as L1, and the distance between the position P3 and the position P4 when the second moving body 26 is in an initial position state (the distance between the second gravity center and the second intersection point in the second moving body 26 when the distance between the second intersection point of the perpendicular line from the rotation center of the rotation axis to the second moving body 26 and the second gravity center of the second moving body 26 is the shortest to be described below) is defined as L2, the following Expressions are satisfied.

$$M1g \sin \phi r1 = M2g \sin \phi r1 \qquad \text{(Expression 1)}$$

$$M1g \cos \phi (L1+r1\theta) = M2g \cos \phi (L2+r1\theta) \qquad \text{(Expression 2)}$$

Here, $\phi$ is the rotation angle of the first moving body 24 from the horizontal axis, r1 is the radius of the pinion 30, and $\theta$ is the rotation angle of the pinion 30. The initial states of the first moving body 24 and the second moving body 26 are brought into a state where the linear motion of the third joint 11 is most shortened. From this, the distance L1 is the shortest distance between the position P1 and the position P2, and the distance L2 is the shortest distance between the position P3 and the position P4.

Additionally, the length L1 and the length L2 are the same unit system, and the mass M1 and the mass M2 are the same unit system.

Expression 1 and Expression 2 are solved, and the mass of the weight 27 and the distance L2 are set so as to satisfy M2=M1 and L2=L1.

It is desirable that the gravity center position of a gross mass M3, not included in the mass M1 and the mass M2, of the holding member 21 and the first guide 22, the second guide 23, the coupling portion 29, an encoder 20a, and the like fixed without being moved with respect to the holding member 21 be at the position of the rotational axis (coincide with the shaft body 31 in the present embodiment) of the second joint 9, and the shape of the holding member 21 be adjusted to adjust the gravity center position.

Accordingly, since a moment around the pinion 30 is balanced with a moment around the axis of the second joint 9, the position of the object A is movable without being influenced by self-weight irrespective of the movement distance of the first moving body 24 and the rotational amount of the second joint 9.

In the present embodiment, a brake that applies slight resistance to advancing and retreating movement of the first moving body 24 may be provided at the linear driving mechanism 20 if necessary. As the brake, for example, a brake that generates sliding resistance between the holding member 21 (refer to FIG. 4) or the first guide 22 and the first moving body 24, a brake that generates sliding resistance between the pinion 30 and the shaft body 31, a brake that generates sliding resistance between the holding member 21 or the second guide 23 and the second moving body 26, or a brake, a friction clutch, or the like that generates sliding resistance between the first moving body 24 and the second moving body 26 can be appropriately selected and adopted. Accordingly, an error can be absorbed even if the balance between the moments N1 and N2 of the forces is slightly lost.

As shown in FIGS. 1 and 2, the grip unit 40 has a gripping portion 41 gripped by the operator Op, and an opening and closing switch portion 42 used for the operation of a surgical instrument 51 to be described below. For example, the opening and closing switch portion 42 opens and closes forceps pieces when forceps are attached as the surgical instrument 51 and controls energization to a high-frequency knife when the high-frequency knife is attached as the surgical instrument 51. In this way, an operation corresponding to a surgical instrument is input by the switch portion 42.

Additionally, sensors for detecting the movement distances and positions of the respective joints and the third joint 11 are attached to the operation unit 4. For example, as shown in FIG. 4, the first joint 6 is provided with an encoder 6a for detecting the rotational amount of the first arm 8 with respect the base 5. Additionally, the third joint 11 is provided with an encoder 20a for detecting the movement distance of the first moving body 24 with respect to the holding member 21.

As shown in FIG. 1, the slave manipulator 50 is connected to the master operation input device 2 via the control unit 52, and is actuated at least on the basis of movement distances or positions detected in the respective encoders (for example, the encoders 6a and 20a shown in FIG. 4) provided at the operation unit 4.

The slave manipulator 50 includes a surgical instrument 51 that operates according to the operation in the master operation input device 2. As the surgical instrument 51, for example, an endoscope, a treatment tool for an endoscope, medical equipment or a medical instrument for performing surgery with respect to the patient P, or the like can be appropriately selected and adopted if necessary.

As shown in FIG. 1, the control unit 52 has a master-side control unit 52a provided at the master operation input device 2 and a slave-side control unit 52b provided at the slave manipulator 50.

The master-side control unit 52a has a position and orientation detector 53 (detector) electrically connected to the respective encoders provided at the operation unit 4 of the master operation input device 2. In the present embodiment, the position and orientation detector 53 is an absolute value type detector, and detects the position and orientation of the operation unit 4 and an input state to the opening and closing switch portion 42 (refer to FIG. 2), on the basis of movement distances from predetermined starting points in the respective encoders.

In the slave-side control unit 52b, the results obtained by detecting the position and orientation of the operation unit 4 and the input state to the opening and closing switch portion 42 in the master-side control unit 52a are input to the slave-side control unit, a signal for actuating the slave manipulator 50 is generated, and the signal is output to the slave manipulator 50 to actuate each surgical instrument 51.

The entire control unit 52 may be disposed at the master operation input device 2, the entire control unit 52 may be disposed at the slave manipulator 50, or the control unit 52 may be installed as separate units at the master operation input device 2 and the slave manipulator 50.

Next, the operation of the third joint 11 of the present embodiment, the master operation input device 2, and the surgery assistance system 1 will be described.

In the present embodiment, as the first moving body 24 protrudes from the holding member 21 and linearly moves as shown in FIG. 4, the distance between the second joint 9 and the fourth joint 12 changes. Since the respective constituent elements ranging from the second arm 13 to the grip unit 40 are attached to the fourth joint 12, the moment of a force on the first moving body 24 side changes according to the protruding amount of the first moving body 24. Here, as the second moving body 26 moves according to the movement distance of the first moving body 24, the weight 27 provided at the second moving body 26 moves in the direction opposite to the movement direction the moving body of the first moving body 24. As a result, the self-weight is compensated for by maintaining a state where the moments of the forces in the linear driving mechanism 20 are balanced with each other. That is, the linear driving mechanism 20 is not influenced by the mass of the object and the linear driving mechanism 20 themselves, and neither rotates around the second joint 9 nor performs extension and retraction unless an external force is applied to the grip unit 40.

As described above, according to the linear driving mechanism with self-weight compensation, the operation input device, and the surgery assistance system 1 of the present embodiment, the state where the moments of the forces are maintained with each other is maintained irrespective of the position of the second joint 9 and the linear motion position of the first moving body 24 in the third joint 11. Moreover, since balance can be achieved with one weight 27 with respect to both the rotation around the second joint 9 and the extension and retraction of the linear driving mechanism 20, the configuration can be made simple, and the operation input device can be made lightweight and small-sized while it is possible to precisely compensate for the self-weight.

Additionally, since the first moving body 24 and the second moving body 26 linearly move in the directions that are parallel to each other and opposite to each other, the first moving body 24 and the second moving body 26 do not interfere with each other during the movement of the first moving body 24 and the second moving body 26.

Additionally, since a so-called rack and pinion mechanism is constituted by the first moving body 24, the second moving body 26, and the coupling portion 29, the movement of the first moving body 24 is reliably transmitted to the second moving body 26, and the self-weight is precisely compensated for.

(Modification Example)

Figure 6:
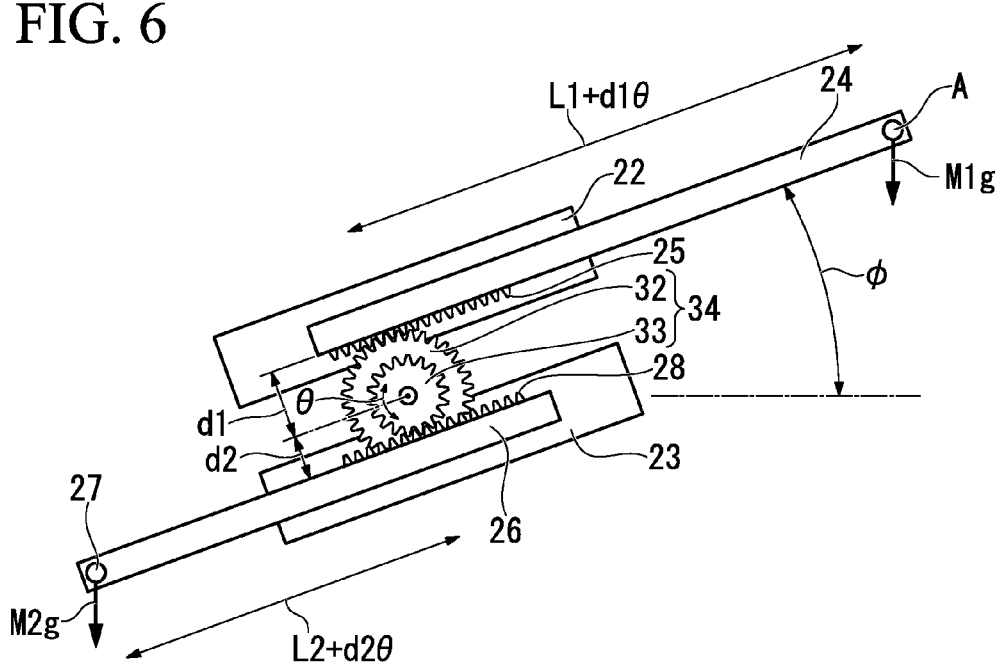
FIG. 6 is a schematic view illustrating the configuration of a modified example of the embodiment of the first embodiment of the present invention.

Next, a modified example of a linear driving mechanism (the third joint 11) with self-weight compensation of the present embodiment will be described. FIG. 6 is a schematic view illustrating the configuration of the present modified example.

In the present modified example, a gear unit 34 having a first gear 32 that engages with the rack 25 of the first moving body 24 and a second gear 33 that engages with the rack 28 of the second moving body 26 and has a smaller radius than that of the first gear 32 is provided as a gear unit that engages with the racks 25 and 28. The first gear 32 and the second gear 33 are coupled to each other so as to rotate around the same rotational axis.

In the present modified example, the movement distance of the second moving body 26 is smaller than the movement distance of the first moving body 24. As a result, the protruding amount of the second moving body 26 from the holding member 21 in the linear driving mechanism 20 is small, and the third joint 11 can be miniaturized.

In this case, the mass of the weight 27 attached to the second moving body 26 is set so that torques are balanced with each other as shown in the following Expressions 1 and 2.

$$M1g \sin \phi d1 = M2g \sin \phi d2 \quad \text{(Expression 1)}$$

$$M1g \cos \phi(L1+d1\theta) = M2g \cos \phi(L2+d2\theta) \quad \text{(Expression 2)}$$

Here, $\phi$ is the rotation angle of the first moving body 24 from the horizontal axis, d1 is the radius (first radius) of the first gear 32, d2 is the radius (second radius) of the second gear 33, and $\theta$ is the rotation angle of the gear unit 34.

The mass of the weight 27 attached to the second moving body 26 only has to satisfy $M2=(L1/L2)\times M1=(d1/d2)\times M1$ from the above Expressions 1 and 2.

Accordingly, since a moment around the gear 34 is balanced with a moment around the axis of the second joint 9, the position of the grip unit 40 is not influenced by self-weight irrespective of the movement distance of the first moving body 24 and the rotational amount of the second joint 9, and the position of the grip unit 40 can be appropriately input.

For example, if M2 is made to be a mass twice as much as M1 when setting d1:d2=L1:L2=2:1, the protruding amount of the second moving body 26 from the holding member 21 can be suppressed to the half of the movement distance of the first moving body 24. As a result, the collision with the second moving body 26 and the base 5 can be avoided, and the operating range of the grip unit 40 of the operation input device can be increased while miniaturizing the device.

(Second Embodiment)

Figure 7:
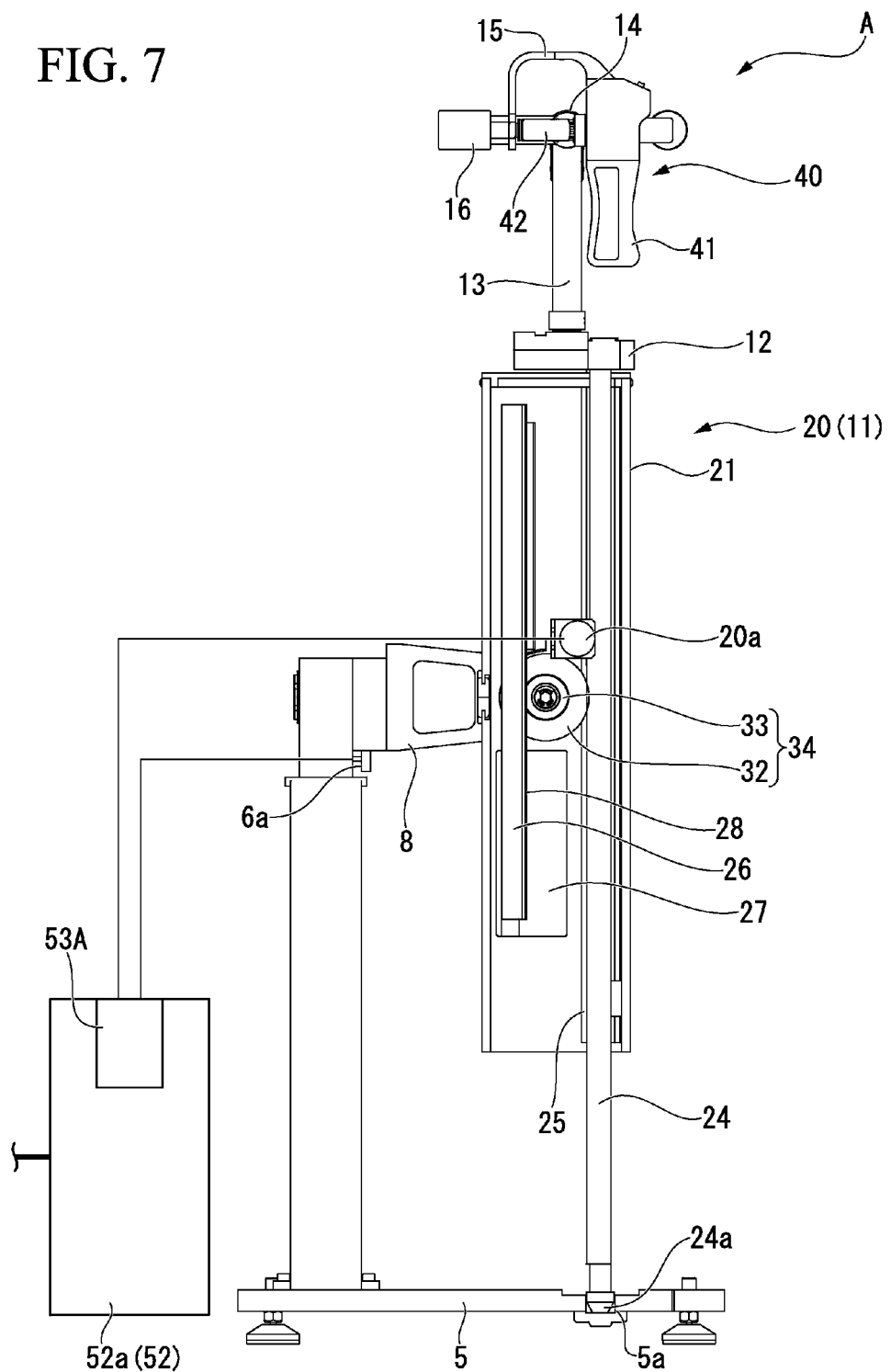
FIG. 7 is a schematic view illustrating an operation input device of a second embodiment of the present invention.

Next, an operation input device of a second embodiment of the present invention will be described. In addition, in the embodiment and its medication example to be described below, the same constituent elements as the constituent elements described in the above-described first embodiment will be designated by the same reference numerals, and duplicate description will not be repeated. FIG. 7 is a schematic view illustrating an operation unit in the operation input device of the present embodiment.

In the present embodiment, a relative value type movement distance detector 53A is provided instead of the absolute value type position and orientation detector 53 described in the first embodiment. That is, a movement distance based on a point of time when the movement distance detector 53A is initialized is detected by the movement distance detector 53A referring to the encoders 6a and 20a provided at the third joint 11.

Additionally, the base 5 is provided with an abutment portion 5a capable of abutting against a portion of the first moving body 24. Specifically, a protruding end 24a (an end opposite to the side where the fourth joint 12 is provided) of the first moving body 24 that protrudes from the linear driving mechanism 20 is enabled to abut against the abutment portion 5a of the base 5. The abutment portion 5a provided at the base 5 and the protruding end 24a of the first moving body 24 have such a concavo-convex shape that the abutment portion and the protruding portion are fittable to each other.

Since the first moving body 24, the second moving body 26, and the coupling portion 29 are coupled to each other, the movement distance detector 53A may not detect the movement distance of the first moving body 24 directly using the encoder 20a. For example, encoders that detect the movement distances of the second moving body 26 and the coupling portion 29 may be used.

If such a configuration is adopted, the relative positions of the base 5 and the linear driving mechanism 20, that is, the joint values of the first joint 6 and the second joint 9 and the position of the first moving body 24 in the third joint 11, are uniquely determined in a state where the protruding end 24a of the first moving body 24 is in contact with the abutment portion 5a.

If the movement distance detector 53A is initialized in a positional relationship in which the first moving body 24 has abutted against the abutment portion 5a, the orientation and extension and retraction amounts of the third joint 11 can be calculated by the movement distance detector 53A, using the positional relationship in which the first moving body 24 has abutted against the abutment portion 5a, as the starting point.

In the present modified example, the starting point can be easily determined with high repeatability by making the protruding end 24a of the first moving body 24 abut against the abutment portion 5a of the base 5 to initialize the movement distance detector.

Additionally, as the protruding end 24a of the first moving body 24 abuts against the abutment portion 5a, the operation input device can be fixed. Thus, the first moving body 24 can be prevented from moving unintentionally in the case of the transportation of the operation input device 4, or the like. As this protruding end 24a is located at the end of the first moving body 24 and the base 5 is arranged at the end of a movable range of the first moving body, the movable range of the operation input device 4 is not narrowed.

(Modification Example)

Next, a modified example of the present embodiment will be described.

In the present modified example, the abutment portion 5a (refer to FIG. 7) of the base 5 is provided with a switch that emits a signal for initializing the movement distance detector 53A. That is, when the positional relationship in which the protruding end 24a of the first moving body 24 has abutted against the abutment portion 5a of the base 5 is brought about, the signal for initializing the movement distance detector 53A is output from the switch to the movement distance detector 53A.

In the present modified example, the starting point can be determined each time the operation input device is used by making indispensable the step of making the protruding end 24a of the first moving body 24 abut against the abutment portion 5a of the base 5 at the beginning of use of the operation input device. Additionally, if the state where the protruding end 24a of the first moving body 24 abuts against the abutment portion 5a of the base 5 is determined as a housed state of the operation input device, the starting point can be determined whenever the operation input device is used, without making the operator Op conscious of the operation for detecting the starting point.

Although the embodiments of the present invention have been described above in detail with reference to the drawings, specific configuration is not limited to the embodiments, and design changes or the like are also included without departing from the scope of the present invention.

For example, in the above-described respective embodiments, the tooth form of the rack and the pinion may be any of a spur gear form, a helical gear form, and a double helical gear form. Additionally, instead of the rack and the pinion, the respective moving bodies may be coupled by a frictional force.

Additionally, the constituent elements shown in the above-described respective embodiments and respective modified examples can be appropriately combined.

In addition, design changes or the like to the above specific configurations are not limited to the above matters.

The invention claimed is:

1. A linear driving mechanism with self-weight compensation comprising:
a holding member that holds:
a first moving body to which an object is attached;
a second moving body provided with a weight; and
a coupling portion that couples the first moving body to the second moving body so that the weight moves along a vector which includes a directional component in a direction opposite to a movement direction of the first moving body;
wherein the holding member is capable of rotating around a rotation axis; and
when a mass of the first moving body in a state where the object is attached is defined as M1, a mass of the second moving body is defined as M2, a distance between a first intersection point of a perpendicular line from a rotation center of the rotation axis to the first moving body and a first gravity center of the first moving body when the distance between the first intersection point and the first gravity center in the first moving body is the shortest is defined as L1, and a distance between a second intersection point of a perpendicular line from the rotation center of the rotation axis to the second moving body and a second gravity center of the second moving body when the distance between the second intersection point and the second gravity center in the second moving body is the shortest is defined as L2, M2=(L1/L2)×M1 is satisfied.

2. The linear driving mechanism with self-weight compensation according to claim 1,
wherein the first moving body and the second moving body linearly move in directions that are parallel to each other and opposite to each other.

3. The linear driving mechanism with self-weight compensation described in claim 1,
wherein the first moving body has a first rack extending in a direction of a straight line connecting the first intersection point and the first gravity center in the first moving body,
wherein the second moving body has a second rack extending in a direction of a straight line connecting the second intersection point and the second gravity center in the second moving body, and
wherein the coupling portion has a gear unit that engages with the first rack and the second rack.

4. The linear driving mechanism with self-weight compensation described in claim 3,
wherein the gear unit has:
a first gear that engages with the first rack; and
a second gear that engages with the second rack,
wherein when a first radius of the first gear is defined as d1 and a second radius of the second gear is defined as d2, M2=(L1/L2)×M1=(d1/d2)×M1 is satisfied.

5. The linear driving mechanism with self-weight compensation according to claim 1,
wherein the rotation center is positioned within a predetermined range from the gravity center of the holding member.

6. An operation input device comprising:
the linear driving mechanism with self-weight compensation according to claim 1;
a base coupled to the linear driving mechanism with self-weight compensation;
an abutment portion that is provided at the base and is capable of abutting against a portion of the first moving body; and
a detector using a relative value form that detects a movement distance of at least one of the first moving body, the second moving body, and the coupling portion,
wherein the detector is initialized in a positional relationship in which the first moving body has abutted against the abutment portion.

7. A surgery assistance system comprising:
the operation input device according to claim 6; and
an actuation unit having a surgical instrument for performing surgery to a patient, the actuation unit being connected to the operation input device, and the actuation unit being actuated on the basis of at least a movement distance or a position detected in the detector.

8. An operation input device comprising:
the linear driving mechanism with self-weight compensation according to claim 1;
a base coupled to the linear driving mechanism with self-weight compensation;
an abutment portion that is provided at the base and is capable of abutting against a portion of the first moving body; and
a detector using a relative value form and that detects a position of at least one of the first moving body, the second moving body, and the coupling portion,
wherein the detector is initialized in a positional relationship in which the first moving body has abutted against the abutment portion.

9. A surgery assistance system comprising:
the operation input device according to claim 8; and
an actuation unit having a surgical instrument for performing surgery to a patient, the actuation unit being connected to the operation input device, and the actuation unit being actuated on the basis of at least a movement distance or a position detected in the detector.

* * * * *